(12) United States Patent
Jensen et al.

(10) Patent No.: US 8,586,374 B2
(45) Date of Patent: Nov. 19, 2013

(54) ANALYSIS DEVICE AND METHOD FOR TESTING THE CATALYTIC ACTIVITY OF SURFACES

(75) Inventors: Jens Dahl Jensen, Berlin (DE); Ursus Krüger, Berlin (DE); Volkmar Lüthen, Berlin (DE); Raymond Ullrich, Schönwalde (DE)

(73) Assignee: Siemens Aktiengesellschaft, Munich (DE)

( * ) Notice: Subject to any disclaimer, the term of this patent is extended or adjusted under 35 U.S.C. 154(b) by 514 days.

(21) Appl. No.: 12/597,030

(22) PCT Filed: Apr. 18, 2008

(86) PCT No.: PCT/EP2008/054760
§ 371 (c)(1),
(2), (4) Date: Oct. 22, 2009

(87) PCT Pub. No.: WO2008/132078
PCT Pub. Date: Nov. 6, 2008

(65) Prior Publication Data
US 2010/0136708 A1      Jun. 3, 2010

(30) Foreign Application Priority Data
Apr. 25, 2007   (DE) .......................... 10 2007 020 544

(51) Int. Cl.
*G01N 21/00* (2006.01)
(52) U.S. Cl.
USPC ........................... 436/164; 422/50; 422/82.05
(58) Field of Classification Search
None
See application file for complete search history.

(56) References Cited

U.S. PATENT DOCUMENTS

| 3,901,600 A | 8/1975 | Johnson, Jr. et al. ............ 356/88 |
| 4,750,133 A | 6/1988 | Eiskamp et al. ............... 364/497 |
| 6,998,991 B1 | 2/2006 | Goldstein et al. ............. 340/628 |

FOREIGN PATENT DOCUMENTS

| EP | 1876439 A1 | 1/2008 | ............. G01N 21/59 |
| WO | 2006/118347 A1 | 9/2006 | ................ G01J 5/58 |

OTHER PUBLICATIONS

Burgi, T. et al. Attenuated Total Reflection Infrared Spectroscopy of Solid Catalysts Functioning in the Presence of Liquid-Phased Reaction, 2006, Advances in Catalysis, vol. 50, pp. 227-283.*
Zenki, M. et al. Repetitive determination of chloride using the circulation of the reagent solution in closed flow-through system, 2002, Talanta, vol. 58, pp. 1055-1061.*
Rupprechter, et al., "Spektroskopie an Modellkatalysatoren unter Atmosphärendruck", Tätigkeitsbericht 2005 der Max-Planck-Geselleschaft, pp. 193-201, 2005
International PCT Search Report, PCT/EP2008/054760, 3 pages, Mailed Sep. 1, 2008.

* cited by examiner

*Primary Examiner* — Robert Xu
(74) *Attorney, Agent, or Firm* — King & Spalding L.L.P.

(57) ABSTRACT

In an analysis device and a method for testing the catalytic activity of surfaces, a reaction cell is provided that has a recess for a sample that is provided with the catalytic surface. In the analysis device, an optical test of the reaction occurring in the reaction cell may occur. The reaction cell has a closed channel that is part of a fluid circuit. The reaction cell may be advantageously designed in a very space-saving manner in its scale, such that a portable use of the analysis cell is possible as well. Here, a simple measurement process of the absorption capacity of the sample fluid located in the reaction cell is conducted. To this end, a laser diode is provided, the measurement stream of which is directed into the reaction cell and reflected multiple times. The light intensity is measured by means of a photodetector.

7 Claims, 2 Drawing Sheets

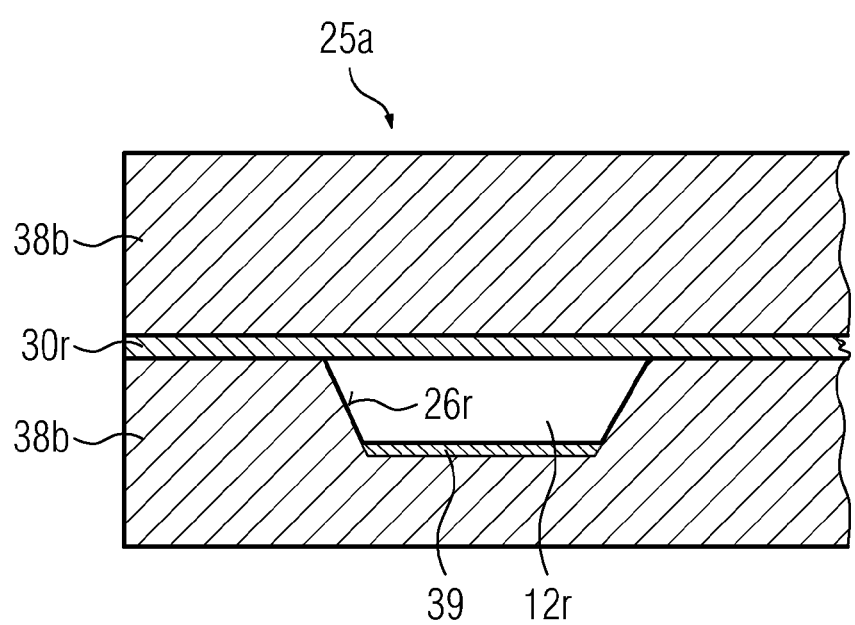

US 8,586,374 B2

ANALYSIS DEVICE AND METHOD FOR TESTING THE CATALYTIC ACTIVITY OF SURFACES

CROSS-REFERENCE TO RELATED APPLICATIONS

This application is a U.S. National Stage Application of International Application No. PCT/EP2008/054760 filed Apr. 18, 2008, which designates the United States of America, and claims priority to German Application No. 10 2007 020 544.0 filed Apr. 25, 2007, the contents of which are hereby incorporated by reference in their entirety.

TECHNICAL FIELD

The invention relates to an analysis device for studying the catalytic activity of surfaces, comprising a reactor cell (or reaction cell) having a compartment for a sample provided with the catalytically active surface and a measuring arrangement for optically studying the reactions taking place in the reactor cell.

BACKGROUND

An analysis device of the type indicated in the introduction is described for example in Rupprechter, G et al., "Spectroskopie an Modellkatalysatoren unter Atmosphärendruck" [spectroscopy on model catalysts at atmospheric pressure], Activity Report 2005 of the Max-Planck Gesellschaft on pages 193 to 201. In order to study the catalytically active surface, a reaction cell is provided into which the relevant sample can be transferred. It is then possible to study this sample in situ by recording spectra with the aid of sum frequency laser spectroscopy (SFG) or polarization-modulation infrared reflection-absorption spectroscopy (PM-IRAS) and interpreting these spectra suitably. Information can thereby be found about the mode of action and effectiveness of the model catalysts. The application of said spectroscopic methods requires an experimental laboratory setup.

SUMMARY

On the basis of this, according to various embodiments, an analysis device for studying the catalytic activity of surfaces can be provided, with which portable use is possible so that even catalyst layers which are being utilized can be subjected to a study on site.

According to an embodiment, an analysis device for studying the catalytic activity of surfaces may comprise a reactor cell having a compartment for a sample provided with the catalytically active surface and a measuring arrangement for optically studying the reactions taking place in the reactor cell, wherein the reaction cell consists of a closed channel which forms part of a fluidic circuit, and wherein the measurement arrangement comprises a light source for generating a measurement beam and a light sensor for this measurement beam, the measuring arrangement allowing the measurement beam to be introduced into the channel and allowing the measurement beam to emerge from the channel in such a way that the measurement beam is reflected at least once by the wall of the channel.

According to a further embodiment, the compartment may be fitted in the wall of the channel so that a sample inserted into the compartment forms a part of the wall of the channel. According to a further embodiment, the channel can be formed by two housing halves having mutually opposing plane connection surfaces. According to a further embodiment, in addition to the reactor cell, a reference reactor cell can be provided which comprises a similar flow geometry to the reactor cell.

According to another embodiment, in a method for studying the catalytic activity of surfaces by using an analysis device, a sample provided with the catalytically active surface is fitted into a compartment of a reactor cell and the reactions taking place in the reactor cell are optically studied by a measuring arrangement, wherein the reactor cell consists of a closed channel which forms part of a fluidic circuit, a fluid containing the educts of the reaction to be catalytically studied being circulated in the circuit, and a measurement beam is generated by a light source in the measuring arrangement, the measurement beam is introduced into the channel, the measurement beam is reflected at least once by the wall of the channel, the measurement beam emerges from the channel and the measurement beam strikes a light sensor.

According to a further embodiment, a measurement value generated by the light sensor may be evaluated in respect of its intensity. According to a further embodiment, the signal may be compared with a reference value which represents a particular status of the analysis device, in particular the status of the channel when it is provided with a fresh sample under particular reaction conditions. According to a further embodiment, the signal may be compared with a reference value which is determined synchronously with the measurement value in a reference reaction cell, the reference reaction cell differing from the reaction cell in respect of a particular reaction parameter. According to a further embodiment, the reference reaction cell may differ from the reaction cell in that a reference sample without catalytic properties or with catalytic properties differing from the other sample for the reaction to be studied is used in it.

BRIEF DESCRIPTION OF THE DRAWINGS

Further details of the invention will be described below with the aid of the drawing. Drawing elements which are the same or correspond to one another are respectively provided with the same references in the figures, these being described again only when differences occur between the individual figures, in which:

FIG. 3 shows another exemplary embodiment of the channel of the analysis device in cross section.

DETAILED DESCRIPTION

Figure 1:
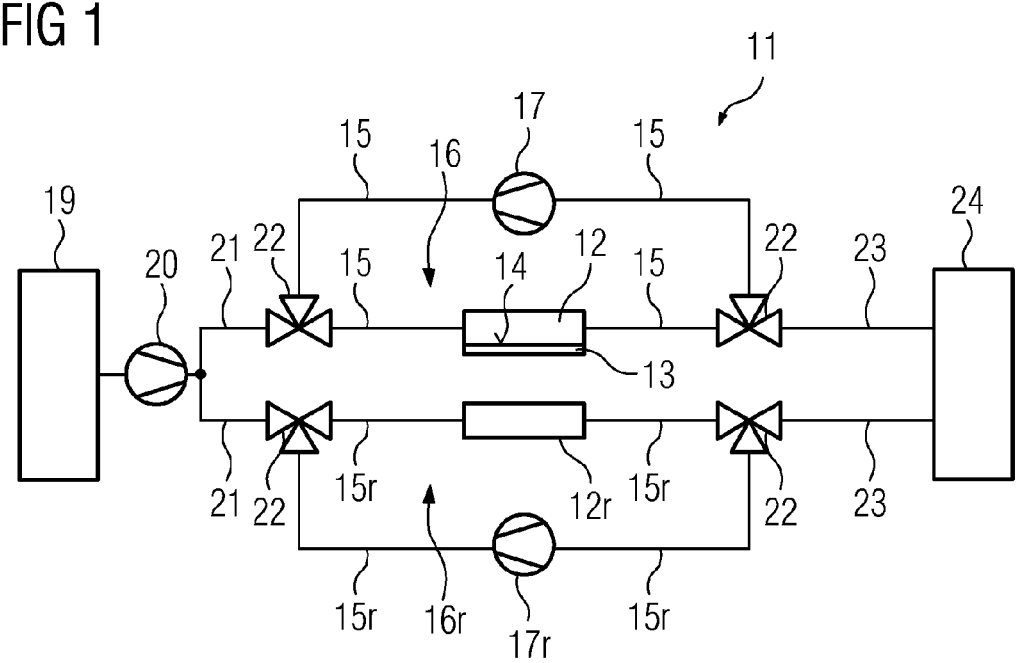
FIG. 1 shows an exemplary embodiment of the analysis device as a block diagram.

With an analysis device as specified in the introduction, according to various embodiments, the reaction cell consists of a closed channel which forms part of a fluidic circuit, and the measurement arrangement comprises a light source for generating a measurement beam and a light sensor for this measurement beam. The measuring arrangement should allow the measurement beam to be introduced into the channel and allow the measurement beam to emerge from the channel in such a way that measurement beam is reflected at least once by the wall of the channel. Arranging the reaction cell in a closed channel, so as to form a fluidic circuit, advantageously makes it possible firstly to form a comparatively compactly designed reaction space with a small reaction volume. A catalytically supported reaction in the sample medium, which is fed through this reaction cell, can advantageously be conducted with predictable reaction conditions by forming the fluidic circuit, when the sample medium is circulated in the channel. Specifically, this advantageously avoids local saturation effects in the sample medium, which could lead to vitiated measurements.

The measuring arrangement according to various embodiments, with a light source and a light sensor, advantageously permits a comparatively simple measurement which is based on the effect that the absorption behavior of the sample medium is modified by a progressing catalytically supported reaction in the channel. By evaluating a measurement value of the recorded light intensity, generated by the light sensor, guiding the measurement beam through the channel makes it possible to obtain information about the absorption behavior. Owing to the miniaturization achieved for the channel in comparison with conventional reaction chambers, it is necessary to deviate the measurement beam at least once in the channel, and preferably several times, which is achieved by reflection from the channel walls. This advantageously increases the path length travelled by the measurement beam in the sample medium, so that a change in the absorption behavior of the sample medium advantageously has a greater effect on the light intensity in the extracted measurement beam. This allows a more sensitive measurement with the light sensor.

In order to ensure that the measurement beam is guided through the channel in the desired way, the optical conditions prevailing during the measurement should be suitably taken into account. This is because the reflection behavior of the measurement beam in the channel depends to a great extent on the optical density of the sample medium. The latter may be in the form of a liquid or gas, and in both cases it is necessary to ensure a suitable refractive index on the channel wall for total reflection of the measurement beam. It is also necessary to ensure that the measurement beam is input into the channel and extracted from it. At least at the entry point of the measurement beam into the channel and its exit point from the channel, the channel wall must be made of an optically transparent material which makes it possible to transmit the measurement beam. In order to compensate for the refraction effects occurring in this case, prisms which provide an optical connection to the light sensor and the light source may respectively be arranged at the entry and exit points for the measurement beam.

The described structure of the analysis device according to various embodiments advantageously provides the possibility of a very compact design. This allows portable use of the analysis device. In particular by measuring the absorption, optionally while taking the time profile into account, the measurement method used makes it possible to obtain information about the catalytic activity of the catalyst being studied. It is therefore possible to identify a loss of catalytic action of the surface due to progressive use, and replace the catalyst when its effectiveness is less than a particular value. The catalyst in use is in this case the sample to be studied by the analysis device.

According to one configuration, the compartment is fitted in the wall of the channels so that a sample inserted into the compartment forms a part of the wall of the channel. This advantageously allows a particularly compact structure because the sample does not need to be entirely contained in the reaction cell, but instead forms an interface of it.

According to another configuration, the channel is formed by two housing halves having mutually opposing plane connection surfaces. This advantageously facilitates production of the housing forming the channel. In particular, the channel may be produced micromechanically (for example by etching or micromilling) in one of the housing halves in the connection surface provided. This makes it clear that the term housing halves is to be interpreted in the widest sense, the only crucial design feature for the housing half being that it provides a plane connection surface. In the case of catalyst surfaces applied over a large area, for example, it is possible for the catalyst as the sample to form one housing half while the analysis device is entirely fitted in the other housing half. This other housing half will also contain the channel formed in the connection surface, so that a closed channel for studying the catalytic surface is not created until the connection surface is fitted onto the catalyst.

A particularly advantageous configuration of the analysis device is obtained when, in addition to the reactor cell, a reference reactor cell is provided which comprises a similar flow geometry to the reactor cell. In the context of the invention, flow geometry is intended to mean those design features of the reactor cell which influence the profile of the flow of the sample medium. Examples which may be mentioned for this are the profile of the fluidic circuit and the available flow cross section. The flow geometries of the reactor cell and reference reactor cell are also comparable in particular when the profiles of the two reactor cells are arranged mirror-symmetrically. This has advantages in particular for a central supply or discharge of the sample medium.

According to other embodiments, in a method for studying the catalytic activity of surfaces by using an analysis device, a sample provided with the catalytically active surface is fitted into a compartment of a reactor cell and the reaction taking place in the reactor cell is optically studied by a measuring arrangement. Such a method is described in the Activity Report 2005 of the Max-Planck Gesellschaft, already mentioned in the introduction, and has already been explained in the introduction.

According to various other embodiments, a method for studying the catalytic activity of surfaces can be provided, which can be operated with comparatively little spatial and equipment outlay and is therefore also suitable for portable use.

With said method, this object is achieved according to various embodiments in that the reactor cell consists of a closed channel which forms part of a fluidic circuit, a fluid containing the educts of the reaction to be catalytically studied being circulated in the circuit. A measurement beam is generated by a light source in the measuring arrangement, and the measurement beam is introduced into the channel and reflected at least once by the wall of the channel; the measurement beam then emerges from the channel and strikes a light sensor.

The explained guiding of the measurement beam is advantageously possible with comparatively simple design means. Only a light source and light sensor are necessary, these having to be arranged suitably in the vicinity of the channel. For guiding the measurement beam, it is furthermore necessary to ensure that the respective refractive indices at the transitions of the optical media (environment, material of the channel wall and sample medium inside the channel) ensure transmission or reflection of the measurement beam, as appropriate. Owing to the simple structure of the analysis device, it can be produced with a sufficiently small overall size so that it can also be employed for portable use. This will make it possible, for example, to study catalytically active surfaces which are in use, in order to identify operationally induced reduction of the catalytic effect of these surfaces.

According to one configuration of the method, a measurement value generated by the light sensor is evaluated in respect of its intensity. The basis for this type of evaluation is the aforementioned relation that the absorption behavior of the sample medium changes with progressing catalytically supported reaction, so that the intensity of the measurement signal recorded by the light sensor also varies as a result of this. The light intensity of the measurement signal thus provides information about the reactions taking place in the channel. A prerequisite for this is that the dependency of the change in the absorption behavior on the quantitative, catalytically induced material conversion should be known. This may, for example, be found from empirical values in serial use of catalysts. With this precondition, the signal may advantageously be compared with a reference value which represents a particular status of the analysis device, in particular the status of the channel when it is provided with a fresh sample under particular reaction conditions. The reference value is generated from the aforementioned empirical value and then provides information about the status of the catalytic surface after the measurement has been carried out. In this case, a further empirical value may be formed as a limit value which indicates the need to replace the catalytic surface.

Another possibility consists in comparing the signal with a reference value which is determined synchronously with the measurement value in a reference reaction cell, the reference reaction cell differing from the reaction cell in respect of a particular reaction parameter. The procedure just described, with the aid of a reference reaction cell, is suitable in particular when empirical values are not yet available for the type of catalyst being used. This is because the reference reaction cell can be used to generate a comparative value so as to provide at least qualitative information about the processes in the reaction cell with the catalyst being studied.

Depending on the information intended to be determined, various reaction parameters of the reference reaction cell may be modified. For example, sample media with different concentrations of the educts may be used.

A particularly favorable application of the reference reaction cell is, however, obtained when it differs from the reaction cell in that a reference sample without catalytic properties or with catalytic properties differing from the other sample for the reaction to be studied is used in it. For the case in which the sample does not have catalytic properties, a reference value which is entirely independent of any catalytic effect can be generated for the absorption in the sample medium. In this way, it is possible to determine possible variations in the absorption behavior which are generated for example owing to varying reaction conditions (temperature, pressure), in which case these can be eliminated from the desired measurement results. Another possibility consists in applying a fresh catalytic surface on the reference sample. If a comparable catalytic surface, which has already been used for a prolonged period of time, is then employed as the sample, it is possible to determine changes in the absorption behavior as a function of the reaction time in relation to the fresh reference sample, which provide information about a possible loss of the catalytic action of the sample.

An analysis device 11 comprises a channel 12, explained in more detail below and only indicated in FIG. 1, in which a sample 13 with a catalytically active surface 14 is fitted. With further lines 15, the channel 12 forms a fluidic circuit 16 in which a preferably liquid sample medium can be circulated by means of a circulation pump 17. The sample medium contains educts for a reaction, which is intended to be supported or initiated by the catalytically active surface 14.

A reference circuit 16r having a circulation pump 17r, lines 15r and a reference channel 12r is constructed mirror-symmetrically with the circuit 16, no sample being provided in the reference channel 12r.

In order to operate the analysis device 11, the sample medium is taken from a storage container 19 and introduced by means of a feed pump 20 through feed lines 21 into the circuit 16 and the reference circuit 16r. Three-way valves 22 are used for this, which are switched after having filled the circuit 16 and the reference circuit 16r so that said circuits respectively form closed systems. After having carried out the analysis which will be explained in more detail below, the three-way valves are switched again so that the sample medium can now be delivered into a waste container 24 through discharge lines 23.

Figure 2:
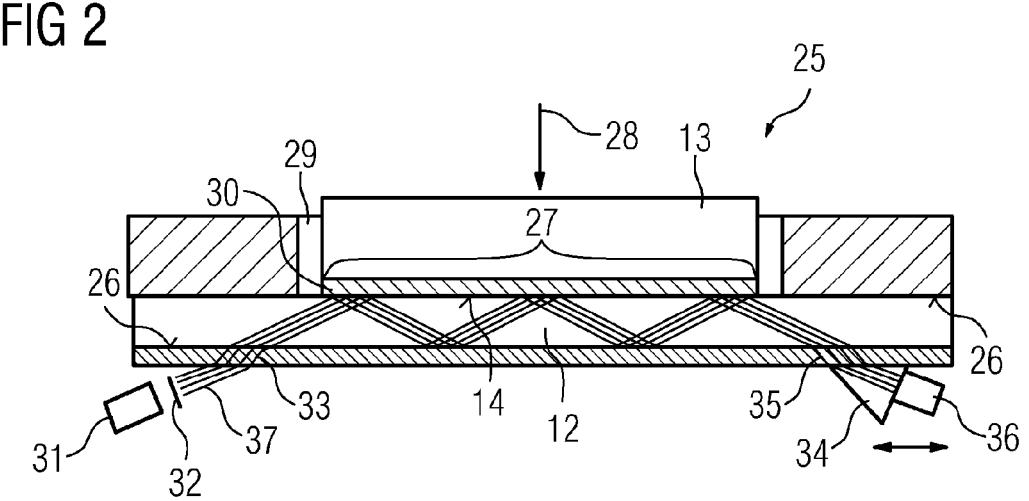
FIG. 2 shows an exemplary embodiment of the channel of the analysis device in longitudinal section, FIG. 2 also representing an exemplary embodiment of the method.

The conduct of the analysis may be explained with the aid of FIG. 2. That part of the circuit 16 which forms a reaction cell 25 is represented. This reaction cell consists of the channel 12, in the wall 26 of which an installation opening 27 for the sample 13 is provided. The sample 13 can be fitted into the installation opening 27 in the direction of the arrow 28 indicated, the installation opening being used as a compartment for the sample 13 and providing a seal 29 to close off the reaction space from the outside. The sample 13 is fitted into the reaction opening so that the catalytically active surface 14 forms a part of the wall 26.

A measuring arrangement which consists of a light source 31, for example a laser diode, an input lens 32 lying at an input position 33 in the emission range of the light source, a prism 34 at an output position 35 and a light source 36, for example a photodetector, is furthermore fastened on the reaction cell 25. The measuring arrangement follows the functional principle given below.

The light source generates a measurement beam 37, which is collimated by means of the input lens 32. At the output position 33, the measurement beam 37 passes through the wall 26 of the channel 12 and is reflected by the wall 26 five times in its longitudinal direction. It subsequently strikes the output position 35 and passes through the wall 26, in order to enter the prism 34. The latter guides the measurement beam 37 into the light sensor 36, with the aid of which the light intensity of the measurement beam 37 can be measured.

FIG. 3 represents another configuration of the housing structure forming the analysis device 11, the region which forms the reference channel 12r being shown here. It is formed by two housing halves 38a, 38b, the cross section of the reference channel 12r being produced for example by anisotropic etching in the housing half 38a. The base of the channel is furthermore provided with a reflection coating 39, which ends in the vicinity of the inlet and outlet positions (not represented in FIG. 3). In the exemplary embodiment according to FIG. 3, the housing half 38b is formed entirely by a reference sample which comprises a reference coating 30r having a catalytically active surface. This therefore differs from the coating 30 (not represented) in that it is fresh and thus does not exhibit any wear phenomena.

What is claimed is:
1. An analysis device for studying the catalytic activity of surfaces, comprising
    a reactor cell comprising a wall having an installation opening receiving a compartment for a sample provided with the catalytically active surface, and
    a measuring arrangement for optically studying the reactions taking place in the reactor cell arranged on the reaction cell opposite said installation opening, wherein
the reactor cell consists of a closed channel which forms part of a fluidic circuit, wherein predictable reaction conditions avoiding local saturation effects are provided by an integration of the reaction cell into the channel of the fluidic circuit, wherein when said compartment is inserted into the installation opening, the catalytically active surface forms a part of the channel wall, and
the measurement arrangement comprises a light source for generating a measurement beam and a light sensor for this measurement beam, the measuring arrangement allowing the measurement beam to be introduced into the channel and allowing the measurement beam to emerge from the channel in such a way that the measurement beam is reflected at least once by the catalytically active surface.

2. The analysis device according to claim 1, wherein the installation opening comprises a seal between opening side walls and the compartment for the sample.

3. The analysis device according to claim 1, wherein in addition to the reactor cell, a reference reactor cell is provided which comprises a similar flow geometry to the reactor cell.

4. An analysis device for studying the catalytic activity of surfaces, comprising
a reactor cell comprising a wall having an installation opening receiving a compartment for a sample provided with the catalytically active surface, the compartment being inserted into the installation opening on one side of the reactor cell, and
a measuring arrangement for optically studying the reactions taking place in the reactor cell, wherein
the reactor cell comprising a channel extending from a left to a right side of the cell and being coupled with a fluidic circuit, wherein predictable reaction conditions avoiding local saturation effects are provided by an integration of the reaction cell into the channel of the fluidic circuit, and
the measurement arrangement being arranged on a reactor cell side opposing said one side comprises a light source for generating a measurement beam and a light sensor for this measurement beam, the measuring arrangement allowing the measurement beam to be introduced into the channel and allowing the measurement beam to emerge from the channel in such a way that the measurement beam is reflected at least once by the catalytically active surface.

5. The analysis device according to claim 4, wherein the compartment is fitted in the wall of the channel so that a sample inserted into the compartment forms a part of the wall of the channel.

6. The analysis device according to claim 4, wherein the compartment comprises a sealing.

7. The analysis device according to claim 4, wherein in addition to the reactor cell, a reference reactor cell is provided which comprises a similar flow geometry to the reactor cell.

* * * * *